US009058801B2

(12) United States Patent
Po et al.

(10) Patent No.: US 9,058,801 B2
(45) Date of Patent: Jun. 16, 2015

(54) ROBUST PROCESS FOR MANAGING FILTER COEFFICIENTS IN ADAPTIVE NOISE CANCELING SYSTEMS

(75) Inventors: Bruce C. Po, Foster City, CA (US); Guy C. Nicholson, Cupertino, CA (US)

(73) Assignee: Apple Inc., Cupertino, CA (US)

( * ) Notice: Subject to any disclaimer, the term of this patent is extended or adjusted under 35 U.S.C. 154(b) by 317 days.

(21) Appl. No.: 13/607,755

(22) Filed: Sep. 9, 2012

(65) Prior Publication Data

US 2014/0072134 A1 Mar. 13, 2014

(51) Int. Cl.
*A61F 11/06* (2006.01)
*G10K 11/178* (2006.01)

(52) U.S. Cl.
CPC .... *G10K 11/1788* (2013.01); *G10K 2210/1081* (2013.01); *G10K 2210/30231* (2013.01); *G10K 2210/3033* (2013.01)

(58) Field of Classification Search
CPC ... G10K 11/178; H04R 3/005; H04R 2460/01
USPC ............................................ 381/71.1, 71.11
See application file for complete search history.

(56) References Cited

U.S. PATENT DOCUMENTS 7,589,631 B2 9/2009 Hovmalm et al.
8,260,612 B2 9/2012 Hetherington
8,515,089 B2 8/2013 Nicholson
2006/0222194 A1* 10/2006 Bramslow et al. ............ 381/314
2007/0076896 A1* 4/2007 Hosaka et al. ............ 381/71.11
2010/0010947 A1 1/2010 Kobayashi
2010/0195839 A1* 8/2010 Barthel et al. .................. 381/60
2010/0296666 A1 11/2010 Lin
2011/0129098 A1* 6/2011 Delano et al. ............. 381/71.11
2012/0140943 A1 6/2012 Hendrix et al.
2012/0316872 A1 12/2012 Stoltz et al.

OTHER PUBLICATIONS

Kuo, Sen M., et al., "Active Noise Control: A Tutorial Review", Proceedings of the IEEE, vol. 87, No. 6, Jun. 1999, (pp. 943-973).

Lin, Chin E., et al., "A CFXLMS Algorithm with Selection Detector for Active Noise Control System", Industrial Technology, 2005, ICIT 2005, IEEE International Conference Dec. 14-17, 2005, (pp. 137-141).

* cited by examiner

*Primary Examiner* — Paul S Kim
*Assistant Examiner* — Norman Yu
(74) *Attorney, Agent, or Firm* — Blakely, Sokoloff, Taylor & Zafman LLP

(57) ABSTRACT

A system for managing the changing state of an adaptive filter in an active noise control (ANC) system is described. An adaptive filter state storage stores copies of prior states of the adaptive filter. A disturbance detector can detect either normal ambient noise or abnormal ambient noise. An adaptive filter state manager signals that a copy of a current state of the adaptive filter is to be repeatedly written to the state storage, so long as normal ambient noise is being detected. But when abnormal noise is detected, the state manager signals that the adaptive filter be restored to one of its prior states, from the copies stored in the state storage. Other embodiments are also described and claimed.

22 Claims, 6 Drawing Sheets

ROBUST PROCESS FOR MANAGING FILTER COEFFICIENTS IN ADAPTIVE NOISE CANCELING SYSTEMS

FIELD

The embodiments of the invention relate to active noise control or canceling (ANC) systems that feature an adaptive filter and an adaptive controller.

BACKGROUND

An active noise control or canceling (ANC) system helps improve the user's listening experience by striving to produce a quieter environment. An "anti-noise" sound wave is produced in such a way that is intended to destructively interfere with or cancel the ambient or background noise sound that would otherwise be heard by the user. In consumer electronics personal listening devices, such as smartphones and portable audio devices such as tablet computers and laptop computers, the listening device often does not have sufficient passive noise attenuation. For instance, a more confortable loose fitting ear bud provides lesser passive ambient noise reduction than a sealed in-ear one. Also, the user is often moving around with a listening device, e.g. walking or jogging. In the case of a smart phone being used in handset mode (against the ear), different users hold the phone differently against their ear, have varied ear anatomy, and tend to move it around during a phone call. All of these user-specific factors may change the acoustic environment or acoustic loading of the listening device in real-time. As a result, attempts are being made to improve the performance of the ANC system in personal listening devices by making the system adaptive. An adaptive filter and an adaptive controller aim to model the different parts of the acoustic environment surrounding the user, or the various acoustic paths leading to the user's eardrum, and to adapt or change the state of the adaptive filter so as to produce an anti-noise signal that better cancels the offending or unwanted noise.

In situations where the noise to be cancelled has transient characteristics, also referred to here as transient disturbances, the adaptive ANC system often loses its bearings, in that it fails to properly drive the adaptive filter. Examples of such "abnormal noise" include for example a police siren, a sudden wind burst, and a scratch of the housing of the personal listening device. This may cause the adaptive system to "diverge" from a solution to the noise cancellation problem, and thereby produce incorrect anti-noise, which of course leads to poor performance (because the noise is now being heard by the user). Transient disturbances are difficult to cancel in the small confines of personal listening devices, due to there being insufficient distance or time lapse between when the disturbance is picked up by a reference microphone and when the anti-noise should be available to cancel it. Moreover, transient disturbances appear suddenly and typically do not last very long, compared to other "normal" ambient or background noise that is long term and essentially periodic.

SUMMARY

It has been found that since transient noise situations cause the active noise control (ANC) system to make incorrect updates to the filter coefficients or state of the adaptive filter, which leads to the production of the incorrect anti-noise, a robust approach to managing the filter coefficients is needed. An embodiment of the invention is a system for managing the state of an adaptive filter, within an ANC system, which may help improve user experience of the ANC system. The ANC system is automatically prevented from responding in its usual course, upon detecting an abnormal disturbance. The new system includes an adaptive filter state storage that stores copies of the prior states of the adaptive filter. A disturbance detector is also provided. An adaptive filter state manager repeatedly signals that a copy of a current state of the adaptive filter should be written to the state storage, so long as the disturbance detector is detecting normal ambient noise as time passes. But when the disturbance detector detects abnormal noise, the state manager signals that the adaptive filter be restored to one of its prior states (from the copies stored in the state storage). For example, the adaptive filter may be signaled to retreat back to how it was just prior to the disturbance having been detected.

In one embodiment, the state manager freezes an adaptive filter controller or state updater, in response to the disturbance detector having detected abnormal noise. While the adaptive filter controller remains frozen, the ANC system continues to produce anti-noise sound during the abnormal disturbance interval, but using the adaptive filter as configured into a selected one of its prior states. The state manager will then unfreeze the adaptive filter controller when the disturbance detector has detected normal noise.

In one embodiment, the adaptive filter state storage stores each of the copies of the prior states in association with a respective time stamp. This allows the state manager to, for example, select an earlier or older copy from the state storage (that will be used to restore the adaptive filter) when the latency of the disturbance detector is long. If, however, the latency of the disturbance detector is short, then the state manager may select a later or more recent copy from the state storage. For example, if the latency for a particular disturbance detections is 25 milliseconds, then the state manager may decide to select a copy of a prior state that has a timestamp of about 25 milliseconds earlier than the point in time at which the state manager was alerted about the abnormal noise. If, however, the latency of the disturbance detector is 50 milliseconds, then the state manager will likely select a prior state that is time-stamped about 50 milliseconds earlier than the arrival of the abnormal noise alert.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one.

DETAILED DESCRIPTION

Several embodiments of the invention with reference to the appended drawings are now explained. Whenever the shapes, relative positions and other aspects of the parts described in the embodiments are not clearly defined, the scope of the invention is not limited only to the parts shown, which are meant merely for the purpose of illustration. Also, while numerous details are set forth, it is understood that some embodiments of the invention may be practiced without these details. In other instances, well-known circuits, structures, and techniques have not been shown in detail so as not to obscure the understanding of this description.

Figure 1:
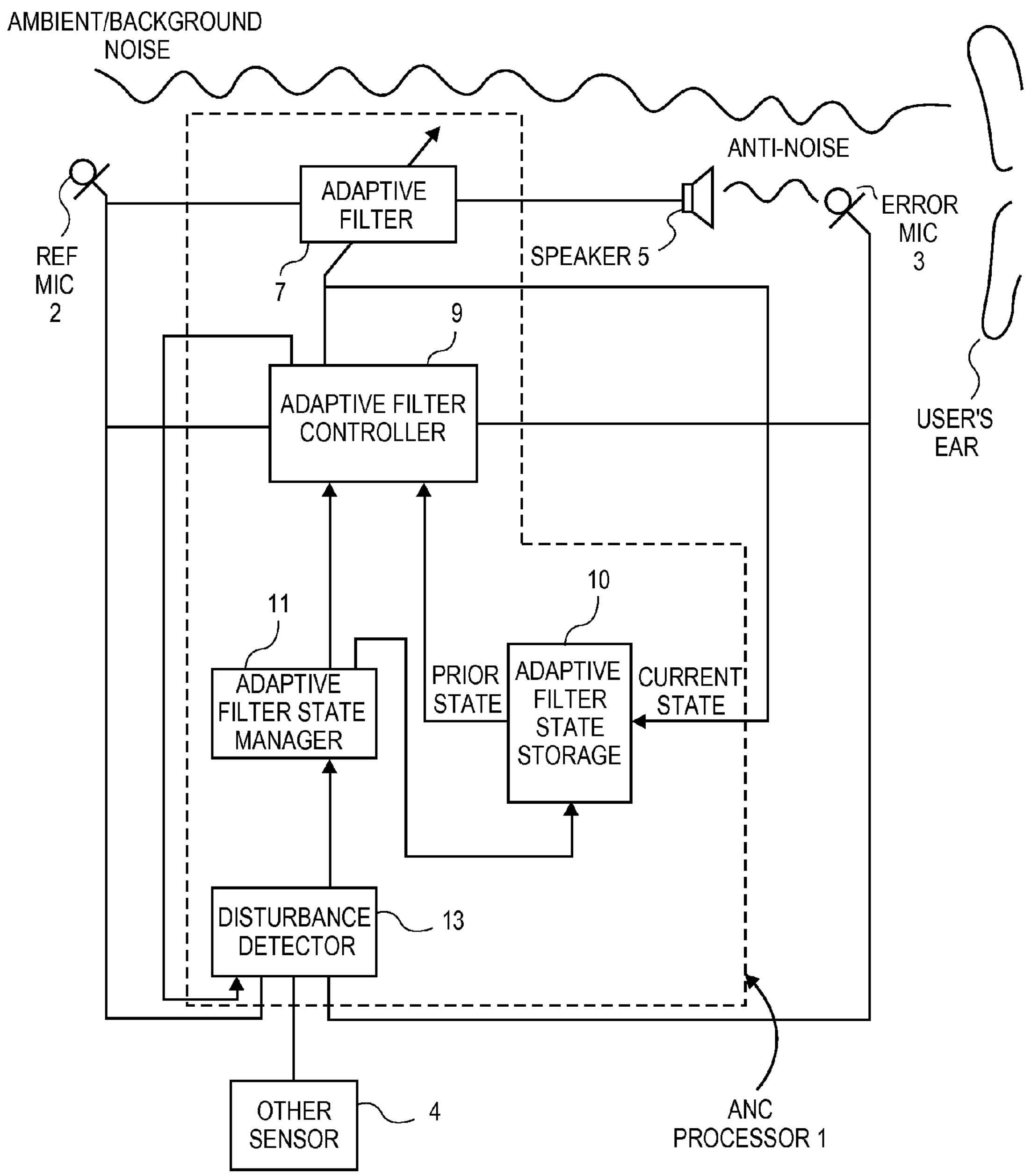
FIG. 1 is a block diagram of an ANC system.

FIG. 1 is a block diagram of an ANC system that contains an ANC processor 1. The ANC processor 1 implements an adaptive active noise cancellation algorithm that continuously and repeatedly updates an adaptive filter 7. The latter models an acoustic system referred to as the primary path for ambient or background noise that reaches an ear of a user, as depicted. This enables the adaptive filter 7 to be used to produce an anti-noise signal that is then driven through the speaker 5. The state of the adaptive filter 7, including its digital filter coefficients, is repeatedly updated by a state updater within an adaptive filter controller 9. The adaptive filter controller 9 may implement a gradient descent algorithm, e.g. least mean squares (LMS), which is designed to find the proper state (digital filter coefficients) that tends to minimize the error between the created anti-noise and the ambient or background noise, as picked up an error microphone 3. Inputs to the adaptive filter controller 9 include digital audio signals from the error microphone 3 and a reference microphone 2. The adaptive filter controller 9 may be part of, for example, a filtered-x LMS adaptive controller engine. Other algorithms for active noise control are alternatively possible. The ANC processor 1 may have further inputs, for example from another sensor for such as a proximity sensor or a position, orientation or movement sensor.

The ANC processor 1 contains an adaptive filter state storage 10, which stores copies of prior states of the adaptive filter 7. The state of the adaptive filter may be defined at least in part by a set of digital filter coefficients, e.g. those of a finite impulse response digital filter that produces a signal from which is derived the anti-noise signal that is driven into the speaker 5. Thus, in one embodiment, the state storage 10 stores copies of prior sets of the digital filter coefficients. The current state of the adaptive filter 7 may be written into the state storage 10 so long as a disturbance detector 13 is detecting normal ambient noise.

The adaptive filter state storage 10 also has an output that produces a copy of a selected one of the prior states that it stores. When the disturbance detector detects abnormal noise, the adaptive filter 7 is to be restored to one of its prior states, from the copies stored in the state storage 10. As described further below, an adaptive filter state manager 11 serves to control the repeated storage of the current state of the adaptive filter 7, and the restoration of the adaptive filter to a prior state.

The disturbance detector 13 may be able to detect normal ambient noise by detecting that a primarily stationary and broad band acoustic disturbance is present. This may be based on an analysis of the audio signals provided by one or more reference microphones 2, the error microphone 3, and a further sensor 4 (e.g., another microphone). The disturbance detector 13 is also able to detect abnormal noise, by detecting a transient acoustic disturbance or a tonal acoustic disturbance. Examples of abnormal noise include for example a musical instrument being played, wind, scratching of the housing in which the reference microphone 2 is located, or extremely high background noise. In one embodiment, the disturbance detector 13 performs high speed digital signal processing (including, for example, spectral analysis and pattern recognition) upon the frames of audio data produced by the reference microphone 2 and optionally by the error microphone 3, as well as digitized data from another sensor 4, in order to detect patterns that are associated with normal ambient noise versus abnormal noise.

In one embodiment, when the disturbance detector 13 is detecting normal ambient noise, the adaptive filter controller 9 is believed to be in a known good state. This known good state may be indicated by for example the adaptive filter controller exhibiting primarily steady state behavior, without any substantial transient behavior, such that it is expected that the adaptive filter coefficients have converged to a solution that may reduce or minimize the error. Yet another approach for detecting normal ambient noise may be to monitor the adaptive filter controller 9 while it is updating the state of the adaptive filter 7 as time passes, to determine that that adaptive filter controller is in a known good state. For example, in a gradient descent adaptive algorithm, the updating of the filter coefficients may be monitored, and if continuous and significant changes are detected it may be assumed that the adaptive system is diverging and possibly becoming unstable, suggesting the presence of abnormal noise.

Turning now to the state manager 11, this block (as introduced above) serves to control when a current state of the adaptive filter 7 is to be written into the state storage 10, and when the adaptive filter 7 should be restored using one of the copies of its prior states (which are stored in the state storage 10). The state manager 11 also has other functions, including that of freezing the adaptive filter controller 9 so that the controller stops updating the state of the adaptive filter 7. This freezing of the state of the adaptive filter 7 may be performed in response to the disturbance detector 13 detecting abnormal noise. In addition, the state manager 11 is able to unfreeze the controller 9, in response to the disturbance detector 13 having detected normal noise. Operation of the state manager 11 in the context of freezing and unfreezing the adaptive filter controller will be described below in connection with FIG. 2.

In another embodiment, the adaptive filter state storage 10 stores each of the copies of the prior states of the adaptive filter 7 in association with a respective time stamp. This allows the state manager 11 to select an earlier copy from the state storage 10 (that will be used to restore the adaptive filter 7) when the latency of the disturbance detector 13 is long, and a later or more recent copy when the latency of the disturbance detector 13 is short.

In a further embodiment, the adaptive filter state storage 10 stores each of the copies of the prior states in association with a flag that indicates whether or not the copy was written while downlink speech of a far-end user was determined to be present. This could be useful in an embodiment where the ANC system is being used within a near-end user device while a voice or videophone call is being conducted with a far-end user (see FIG. 4). Although not shown in FIG. 1, the disturbance detector 13 in that case would have a further input that receives the down link signal—see the downlink audio processor in FIG. 5—which contains speech of the far-end user during the phone call. A voice activity detector (VAD) would then analyze the down link audio signal to provide a binary decision as to whether a given frame of digital audio contains primarily speech or primarily noise. This information, namely whether or not the prior state was captured while down link speech was present, may be used by the state manager 11 to inform its decision as to which one of the prior states to select (for restoring the adaptive filter 7). In this connection, the state manager 11 may be designed to perform a decision making process or a filtering process, when selecting one of the copies of the prior states from the state storage 10. Such a decision making process may involve determining whether or not local speech activity (that is, speech by the near-end user) is present when the disturbance detector 13 indicates abnormal noise, based on which the state manager 11 may select a copy of a prior state that is associated with a flag indicating no far-end user speech.

Figure 2:
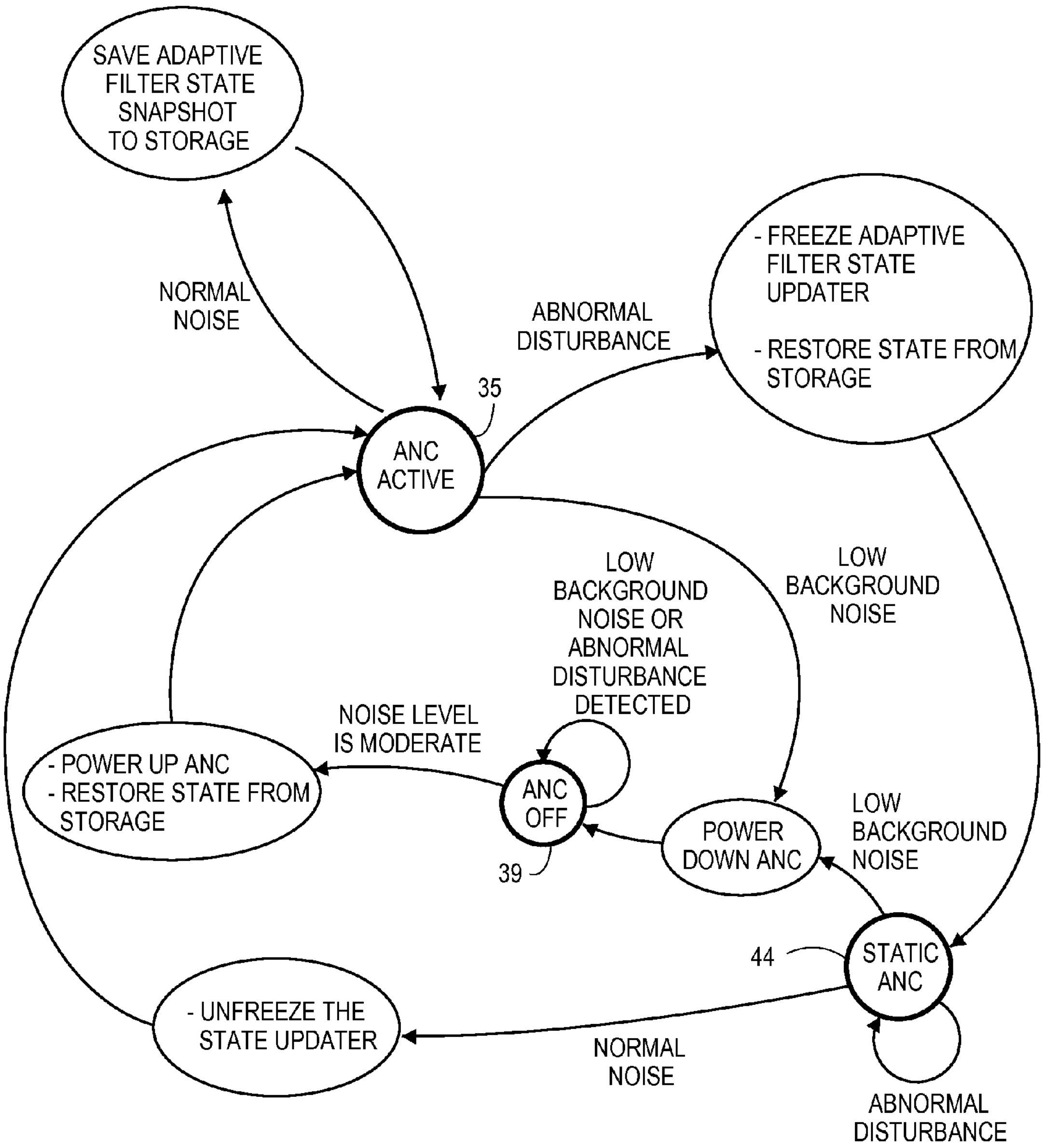
FIG. 2 is a state diagram that may represent an algorithm or process for managing the adaptive filter state, for improved robustness.

Turning now to FIG. 2, a state diagram that may also represent an algorithm or process for managing the state of the adaptive filter 7 for improved robustness is shown. The state diagram may refer to the various states of the ANC processor 1 and may be used to implement a hardware state machine or a programmed processor within the state manager 11. The state manager 11 may thus keep track of the following states: ANC active state 35, ANC off state 39, and static ANC state 44. In the ANC active state 35, the adaptive filter controller 9 has been configured to operate in its usual course, to automatically adapt the state of the adaptive filter 7 based on its measurements of noise through the reference microphone 2, and error through the error microphone 3, and in accordance with a suitable adaptive filter controller engine (e.g., filtered-x LMS). The ANC active state 35 is maintained so long as the disturbance detector 13 is detecting normal noise. Moreover, during ANC active 35, snapshots of the adaptive filter state are saved to storage repeatedly, as time passes. In other words, referring back to FIG. 1, the state manager 11 in concert with the adaptive filter state storage 10 serve to repeatedly write snapshots of the state of the adaptive filter 7 into the storage 10, while normal ambient noise, not abnormal noise, is being detected as time passes. This occurs in the state diagram of FIG. 2 during the ANC active state or mode of operation 35.

In the ANC off state 39, a substantial portion of the ANC processor 1 (see FIG. 1) is powered down or inactivated, for example to save power. Of course in that case, no anti-noise signal is being driven through the speaker 5. The ANC off state is maintained so long as the disturbance detector 13 is detecting very low background noise, or continues to detect an abnormal noise or disturbance. If however the detected noise level is moderate, or normal noise starts to be detected, the state manager 11 transitions from the ANC off state 39 into the ANC active state 35, by first powering up, for example, the adaptive filter controller 9 and the adaptive filter 7, and restoring the state of the adaptive filter 7 from a copy of a prior state in the state storage 10.

The state manager 11 may also have a static ANC state 44. The static ANC state 44 may be entered from the ANC active state 35, upon detection of abnormal disturbance. Here, the state manager 11 signals that the adaptive filter 7 be restored to one of its stored prior states, in response to abnormal noise being detected. In the static ANC state 44, the adaptive filter 7 continues to be used to produce an anti-noise signal that is also driven through the speaker 5, to produce anti-sound, but it does so based on a frozen adaptive filter state. The frozen state may have been restored from a copy of a prior state in the state storage 10 (following the detection of abnormal noise, coming out of the ANC active state 35). The state manager 11 stays in the static ANC state 44 so long as abnormal noise or disturbance is being detected. If, however, relatively low background noise starts to be detected, a transition may be made into the ANC off state 39, based on the understanding that at very low background noise levels, ANC may not be needed to improve the user's listening experience. On the other hand, if normal noise levels start to be detected, then a transition is made to the ANC active state 35, by way of first unfreezing the state updater (unfreezing the adaptive filter controller 9) so that the adaptive filter 7 can start to be updated, in the usual course of the adaptive filter algorithm.

The above described state diagram may yield a more robust ANC processor, because when abnormal disturbances are detected, the ANC processor 1 automatically and immediately transitions into a static ANC mode of operation, by freezing the adaptive filter state updater and restoring the adaptive filter 7 to a "known good state," being a previously captured state of the filter 7, whose copy is stored in the state storage 10. While in the static ANC mode, the performance of the ANC system may not be optimal in that the restored filter state is a model of the acoustic system from a moment ago and not a model of the current acoustic system. However, the ANC processor 1 may find it easier or quicker to adapt when coming out of the abnormal disturbance situation (when normal noise starts to be detected), because at that point the adaptive filter 7 is already configured with a "reasonable" approximation to the ultimate set of digital filter coefficients that it would need to properly cancel the normal ambient or background noise.

Figure 3:
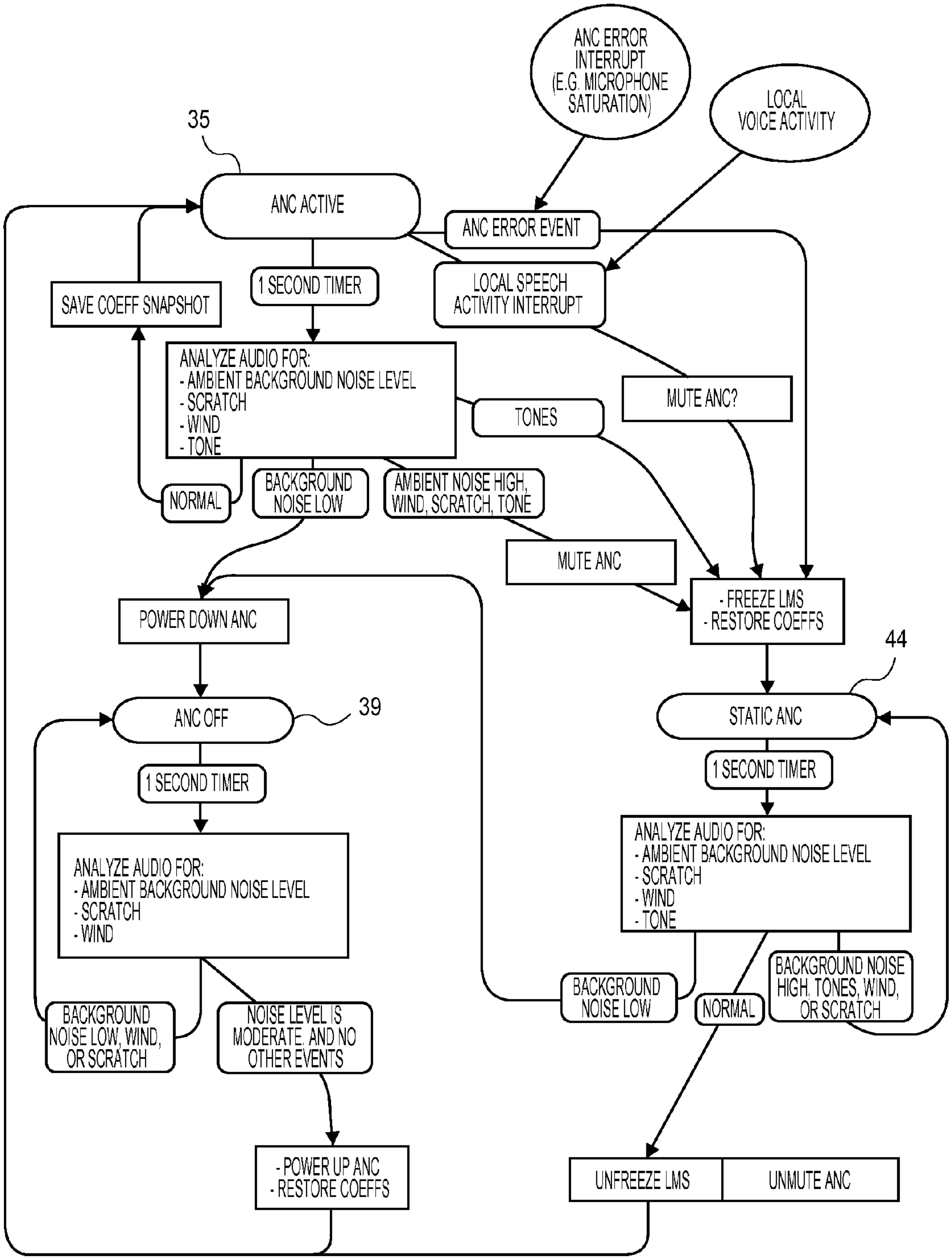
FIG. 3 is a state diagram of another embodiment of the invention, showing specific types of disturbance detections and specific responses to such detections.

FIG. 3 is a state diagram of another embodiment of the invention, showing specific types of disturbance detections and specific responses to such detections. In this embodiment, the same basic states of the ANC processor 1 that were described in FIG. 2 are present, including the ANC active state 35, ANC off state 39 and static ANC 44. Beginning with the ANC active state 35, the processor 1 will remain in this state so long as repeated analysis of detected digital audio reveals ambient background noise level to be normal, and no scratch, wind, local voice activity or tone signals are detected. This analysis may be repeated, for example, every one second, although the particular interval is, of course, adjustable. Snapshots of the digital filter coefficients are routinely saved while in the ANC active state 35, in this example, every one second. Of course, given that the space available within the state storage 10 (see FIG. 1) is limited, in one embodiment, the snapshots of the current state are saved by overwriting the oldest prior state. Other techniques for determining which prior state to overwrite are possible.

The ANC processor 1 may transition from the ANC active state 35 to the ANC off state 39, if very low background noise starts to be detected. This, of course, is followed by a power down operation of the relevant sections of the ANC processor 1 (see FIG. 1).

Still referring to FIG. 3, the transition between ANC active 35 into static ANC 44 may occur in the following scenarios. For example, an ANC error event may trigger this transition, e.g. receiving an error interrupt from one of the sensors, such as a microphone saturation condition. This could suggest that, for example, the ambient noise is too loud for the adaptation algorithm or in view of the anti-noise sound production capability. As in FIG. 2, transition to the static ANC state 44 involves freezing the adaptive filter controller (in this case, freezing an LMS engine), and restoring the digital filter coefficients of the adaptive filter (using one of the copies of the prior states of the adaptive filter stored in the state storage 10).

Other scenarios for the transition from ANC active state 35 to static ANC 44 include the detection of local speech (local speech activity or local voice activity being detected). This covers the situation where, for example, the user of the personal listening device begins talking, such that the need for noise cancellation to that user's ears may not be as strong. In some cases therefore, a decision may also be made to mute the ANC such that no anti-noise sound is produced, in the situation where local voice activity is detected (and a transition is made into the static ANC state).

A transition into static ANC 44 may also occur when the audio analysis reveals tones or, more particularly, narrow band tones (e.g., a siren) or very high ambient noise levels, wind, or scratch. In the latter case, the anti-noise sound production may also be muted or stopped.

When the ANC processor 1 is in the static ANC state 44, the adaptive filter controller may be frozen, or the adaptive filter may be frozen such that it is no longer being updated, but anti-noise sound may continue to be produced in accordance with the frozen state of the adaptive filter. Once again, the detected digital audio from the ref mic and error microphone may be analyzed for ambient background noise level, scratch, wind and tones. The analysis may once again be performed periodically as time passes (on sequential frames of audio), for example, every second. The static ANC state 44 continues so long as the background noise being detected is relatively high, or a tone, wind, or scratch is being detected. This refers to a transient disturbance situation, where the ANC processor 1 is not saving any snapshots of the adaptive filter state to storage, and is not allowed to update the adaptive filter in its usual course. This may help ensure that the adaptive filter is not mis-adapted to a state that is not representative of typical acoustic systems or environments in which the user may find itself. This helps avoid a poor noise cancellation performance situation, and may also avoid an irrecoverable state where the adaptive filter controller may then exhibit difficulty in converging to a proper solution (once the system transitions back to the ANC active state 35).

The system may transition back to the ANC active state 35 when the periodic analysis reveals that a normal background noise level is being detected, which triggers the adaptive filter controller to be unfrozen (unfreeze the LMS engine), and optionally unmute ANC (if ANC had been muted), to enable the anti-noise sound to be produced.

Still referring to FIG. 3, there is one more transition path that is possible out of the static ANC state 44, and that is to the ANC off state 39. Similar to what was described above for the ANC active state 35, the transition from static ANC 44 into ANC off 39 can occur when the background noise level being detected is very low.

Finally, the last state in FIG. 3 is the ANC off state 39, which, of course, corresponds to the situation where the ANC processor may essentially be turned off (except for, of course, the disturbance detector 13, the adaptive filter state manager 11, and the adaptive filter state storage 10). The audio analysis continues in the ANC off state 39, again periodically looking for ambient background noise levels that are very low, wind, or scratch events. In that case, the processor 1 remains in the ANC off state 39. However, if the noise level being detected is moderate (normal noise) then a transition can be made into the ANC active state 35, by powering up the adaptive filter controller and the adaptive filter 7, and restoring the filter 7 with the selected copy of its prior state (digital filter coefficients) taken from the storage 10.

It was described earlier that in the embodiment where the copies of the current state of the adaptive filter are periodically being captured and stored in the state storage 10, that these could also be time stamped. As such, this may allow the state manager 11 to select earlier or later ones of the stored prior states, depending upon the latency associated with the disturbance detector 13. Indeed, it is possible that each of the different possible disturbances that can be detected, namely normal ambient background noise, low ambient background noise, high ambient background noise, tones, wind, and scratch, may have a different, respective latency. These different latencies may be heuristically determined and programmed into the state manager 11. Thereafter, depending upon the detected disturbance, the state manager 11 can perform a table look up for instance to determine the latency associated with the current detection, and then use the time stamp values in the sate storage 10 to find the "closest" prior state, for restoring the adaptive filter.

It should also be noted that in addition to the real-time tracked prior states that are stored in the state storage 10, there may be a default state for the adaptive filter 7 (e.g., a default or fixed set of digital filter coefficients) that may be available for the state manager 11 to choose from when "restoring" the adaptive filter 7.

Figure 4:
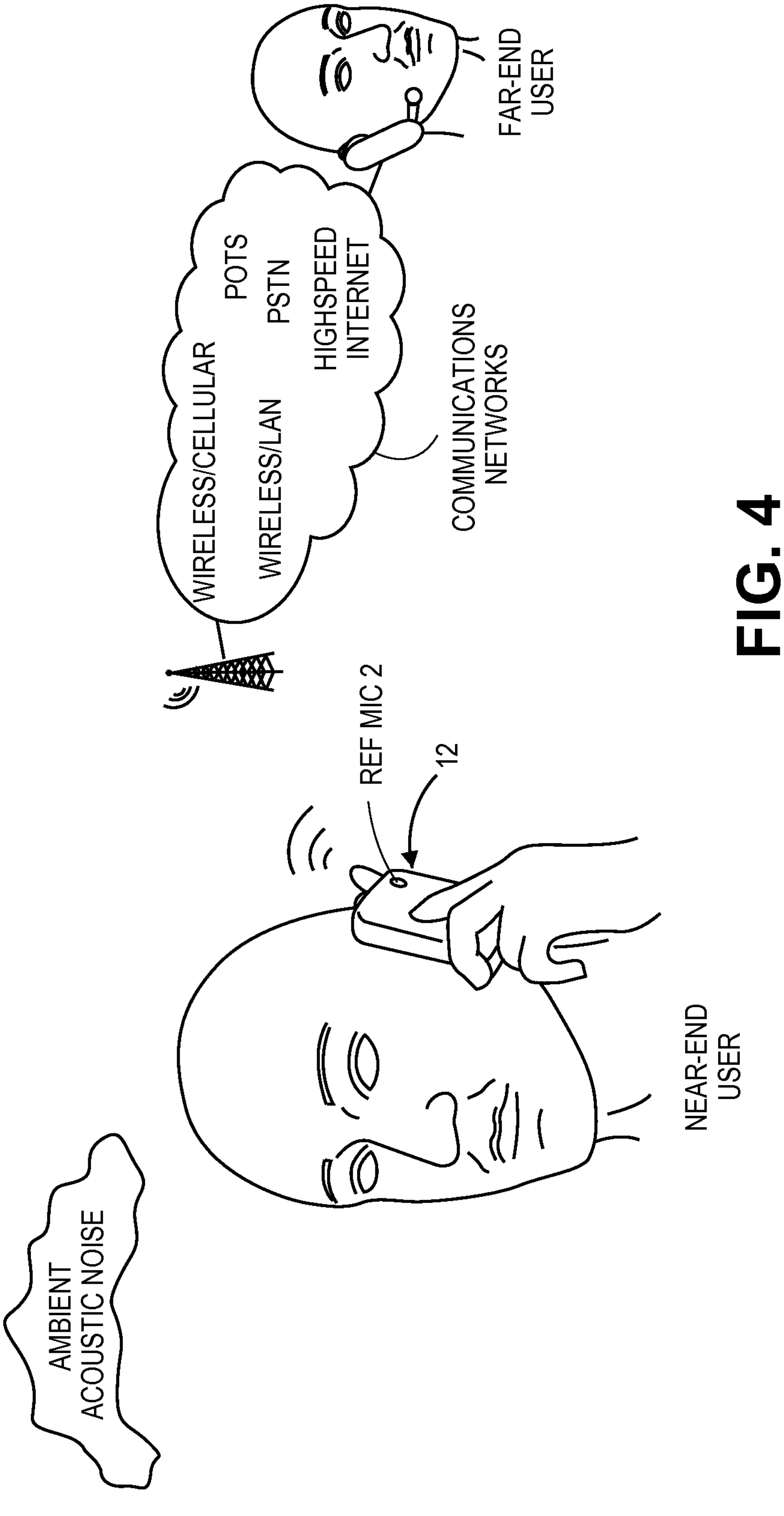
FIG. 4 illustrates an example of an end-user acoustic environment and consumer electronics product application of the ANC system.

FIG. 4 illustrates an example of an end-user acoustic environment and consumer electronics product application of an ANC system. A near-end user is holding a mobile communications handset device 12 such as a smart phone or a multi-function cellular phone. The ANC processor 1, the reference microphone 2 and the error microphone 3 (as well as the related processes described above) can be implemented in such a personal audio device. The near-end user is in the process of a call with a far-end user who is also using a user or personal communications device. The terms "call" and "telephony" are used here generically to refer to any two-way real-time or live audio communications session with a far-end user (including a video call which allows simultaneous audio). The term "mobile phone" is used generically here to refer to various types of mobile communications handset devices (e.g., a cellular phone, a portable wireless voice over IP device, and a smart phone). The mobile device 12 communicates with a wireless base station in the initial segment of its communication link. The call, however, may be conducted through multiple segments over one or more communication networks 3, e.g. a wireless cellular network, a wireless local area network, a wide area network such as the Internet, and a public switch telephone network such as the plain old telephone system (POTS). The far-end user need not be using a mobile device, but instead may be using a landline based POTS or Internet telephony station.

The mobile device 12 has an exterior housing in which are integrated an earpiece speaker (which may be the speaker 5—see FIG. 1) near one side of the housing, and a primary handset (or talker) microphone 6 that is positioned near an opposite side of the housing. The mobile device 12 may also have a secondary microphone (which may be the reference microphone 2) located on a side or rear face of the housing and generally aimed in a different direction than the primary microphone 6, so as to better pickup the ambient sounds.

Figure 5:
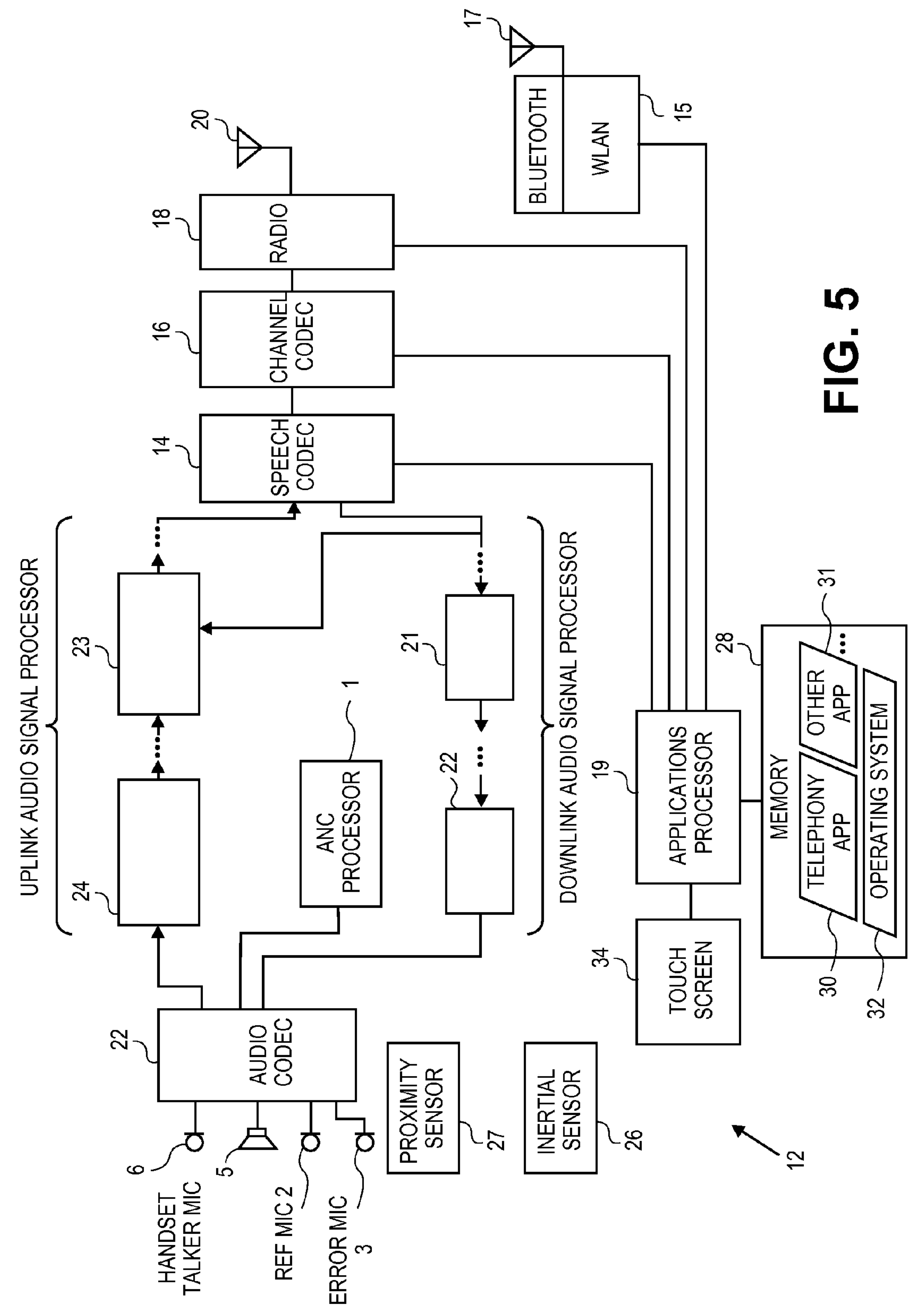
FIG. 5 is a block diagram of some relevant constituent components of a personal mobile communications device such as a smartphone, in which an ANC processor may be implemented.

A block diagram of some of the functional unit blocks of the mobile device 12 is shown in FIG. 5. These include constituent hardware components such as those, for instance, of an iPhone™ device by Apple Inc. Although not shown, the mobile device 12 has a housing in which the primary mechanism for visual and tactile interaction with its user is a touch sensitive display screen (touch screen 34). As an alternative, a physical keyboard may be provided together with a display-only screen. The housing may be essentially a solid volume, often referred to as a candy bar or chocolate bar type, as in the iPhone™ device. Alternatively, a moveable, multi-piece housing such as a clamshell design or one with a sliding physical keyboard may be provided. The touch screen 34 can display typical user-level functions of visual voicemail, web browser, email, digital camera, various third party applications (or "apps"), as well as telephone features such as a virtual telephone number keypad that receives input from the user via touch gestures.

The user-level functions of the mobile device 12 are implemented under the control of an applications processor 19 or a system on a chip (SoC) processor that is programmed in accordance with instructions (code and data) stored in memory 28 (e.g., microelectronic non-volatile random access memory). The terms "processor" and "memory" are generically used here to refer to any suitable combination of programmable data processing components and data storage that can implement the operations needed for the various functions of the device described here. An operating system 32 may be stored in the memory 28, with several application programs, such as a telephony application 30 as well as other applications 31, each to perform a specific function of the device when the application is being run or executed. The telephony application 30, for instance, when it has been launched, unsuspended or brought to the foreground, enables a near-end user of the mobile device 12 to "dial" a telephone number or address of a communications device of the far-end user, to initiate a call, and then to "hang up" the call when finished.

For wireless telephony, several options are available in the mobile device 12 as depicted in FIG. 5. A cellular phone protocol may be implemented using a cellular radio 18 that transmits and receives to and from a base station using an antenna 20 integrated in the mobile device 12. As an alternative, the mobile device 12 offers the capability of conducting a wireless call over a wireless local area network (WLAN) connection, using the Bluetooth/WLAN radio transceiver 15 and its associated antenna 17. The latter combination provides the added convenience of an optional wireless Bluetooth headset link. Packetizing of the uplink signal, and depacketizing of the downlink signal, for a WLAN protocol, may be performed by the applications processor 19.

The uplink and downlink signals for a call that is being conducted using the cellular radio 18 can be processed by a channel codec 16 and a speech codec 14 as shown. The speech codec 14 performs speech coding and decoding in order to achieve compression of an audio signal, to make more efficient use of the limited bandwidth of typical cellular networks. Examples of speech coding include half-rate (HR), full-rate (FR), enhanced full-rate (EFR), and adaptive multi-rate wideband (AMR-WB). The latter is an example of a wideband speech coding protocol that transmits at a higher bit rate than the others, and allows not just speech but also music to be transmitted at greater fidelity due to its use of a wider audio frequency bandwidth. Channel coding and decoding performed by the channel codec 16 further helps reduce the information rate through the cellular network, as well as increase reliability in the event of errors that may be introduced while the call is passing through the network (e.g., cyclic encoding as used with convolutional encoding, and channel coding as implemented in a code division multiple access, CDMA, protocol). The functions of the speech codec 14 and the channel codec 16 may be implemented in a separate integrated circuit chip, some times referred to as a baseband processor chip. It should be noted that while the speech codec 14 and channel codec 16 are illustrated as separate boxes, with respect to the applications processor 19, one or both of these coding functions may be performed by the applications processor 19 provided that the latter has sufficient performance capability to do so.

The applications processor 19, while running the telephony application program 30, may conduct the call by enabling the transfer of uplink and downlink digital audio signals (also referred to here as voice or speech signals) between itself or the baseband processor on the network side, and any user-selected combination of acoustic transducers on the acoustic side. The downlink signal carries speech of the far-end user during the call, while the uplink signal contains speech of the near-end user that has been picked up by the handset talker microphone 6.

The analog-digital conversion interface between the acoustic transducers and the digital downlink and uplink signals may be accomplished by an audio codec 22. The acoustic transducers include an earpiece speaker (also referred to as a receiver) which may be the speaker 5, a loud speaker or speaker phone (not shown), one or more microphones including the talker microphone 6 that are intended to pick up the near-end user's speech primarily, a secondary microphone such as reference microphone 2 that is primarily intended to pick up the ambient or background sound, and the error microphone 3. The audio codec 22 may interface with the ANC processor 1 as shown, in that it outputs or provides the digital audio signals of reference microphone 2 and the error microphone 3 to the ANC processor 1, while receiving the anti-noise signal from the ANC processor 1. The audio codec 22 may then mix the anti-noise signal with the downlink audio (coming from the downlink audio signal processing chain) prior to driving a power amplifier that in turn drives the speaker 5.

The codec 22 may also provide coding and decoding functions for preparing any data that may need to be transmitted out of the mobile device 12 through a peripheral device connector such as a USB port (not shown), as well as data that is received into the mobile device 12 through that connector. The connector may be a conventional docking connector that is used to perform a docking function that synchronizes the user's personal data stored in the memory 28 with the user's personal data stored in the memory of an external computing system such as a desktop or laptop computer.

Still referring to FIG. 5, an audio signal processor is provided to perform a number of signal enhancement and noise reduction operations upon the digital audio uplink and downlink signals, to improve the experience of both near-end and far-end users during a call. This processor may be viewed as an uplink processor and a downlink processor, although these may be within the same integrated circuit die or package. Again, as an alternative, if the applications processor 19 is sufficiently capable of performing such functions, the uplink and downlink audio signal processors may be implemented by suitably programming the applications processor 19.

Various types of audio processing functions may be implemented in the downlink and uplink signal processing paths. The downlink signal path receives a downlink digital signal from either the baseband processor (and speech codec 14 in particular) in the case of a cellular network call, or the applications processor 19 in the case of a WLAN/VoIP call. The signal is buffered and is then subjected to various functions, which are also referred to here as a chain or sequence of functions. These functions are implemented by downlink processing blocks or audio signal processors that may include, one or more of the following which operate upon the downlink audio data stream or sequence: a noise suppressor, a voice equalizer, an automatic gain control unit, a compressor or limiter, and a side tone mixer.

The uplink signal path of the audio signal processor passes through a chain of several processors that may include an acoustic echo canceller, an automatic gain control block, an equalizer, a compander or expander, and an ambient noise suppressor. The latter is to reduce the amount of background or ambient sound that is in the talker signal coming from the primary microphone 6, using, for instance, the ambient sound signal picked up by a secondary microphone (e.g., reference microphone 2). Examples of ambient noise suppression algorithms are the spectral subtraction (frequency domain) technique where the frequency spectrum of the audio signal from the primary microphone 8 is analyzed to detect and then suppress what appear to be noise components, and the two microphone algorithm (referring to at least two microphones being used to detect a sound pressure difference between the microphones and infer that such is produced by noise rather than speech of the near-end user).

Figure 6:
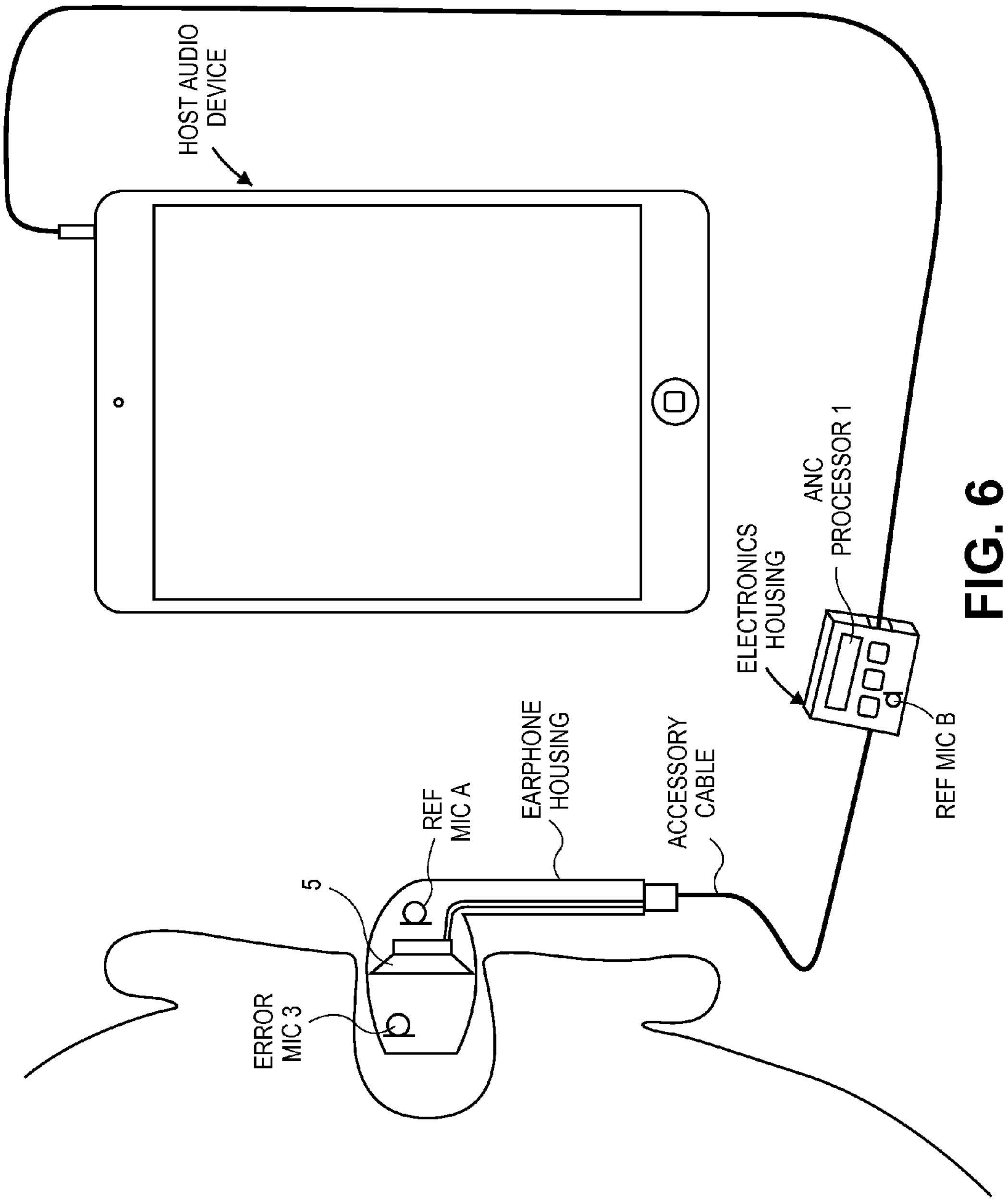
FIG. 6 illustrates another consumer electronic listening product, in which the ANC system may be implemented.

FIG. 6 illustrates another consumer electronic listening product in which an ANC system may be implemented. A host audio device is shown, in this example being a tablet computer, that has a peripheral connector to which a headset is electrically connected via an accessory cable. The headset may include an in-the-ear earphone as shown, having an earphone housing in which the error microphone 3 and the reference microphone 2 (in this example ref mic A) are integrated. The speaker 5 in this case is a small or miniature speaker driver suitable for use within an earphone. In this case, there is a second reference microphone, ref mic B, that is located on the accessory cable somewhere between the earphone housing and the connector that is attached to the host audio device. Communication or signaling wires may connect the error microphone 3, ref mic A, ref mic B, and speaker 5 to the ANC processor 1 which in this case is integrated within a separate electronics housing (separate from the host device housing and the earphone housing) that is attached to the accessory cable. It is expected that the ANC processor 1 together with other electronics within this housing may receive dc power from a power supply circuit within the battery-powered host audio device, via the accessory cable. Other system applications of the ANC system within the realm of consumer electronics personal listening devices are possible.

While certain embodiments have been described and shown in the accompanying drawings, it is to be understood that such embodiments are merely illustrative of and not restrictive on the broad invention. For example, as shown in FIG. 1, the adaptive filter 7 (whose state is to be managed for improved robustness) is located essentially in line between the output of the reference microphone 2 and the input of the speaker 5. This corresponds to a digital filter commonly described as W(z). But the techniques described above for managing the filter coefficients of an adaptive filter may also be applicable to control the changing state of other adaptive filters within an ANC processor 1. For example, in the filtered-x LMS approach, an adaptive filter Se(z), which models the secondary path or sometimes referred to as the acoustic cancellation path (between the speaker 5 and the error microphone 3) can be similarly managed. Accordingly, the invention is not limited to the specific constructions and arrangements shown and described, since various other modifications may occur to those of ordinary skill in the art.

What is claimed is:

1. A system for managing the changing state of an adaptive filter in an active noise control (ANC) system, comprising:

an adaptive filter state storage that is to store copies of prior states of the adaptive filter;

a disturbance detector;

an adaptive filter state manager that is to a) signal that a copy of a current state of the adaptive filter be repeatedly written to the state storage so long as the disturbance detector is detecting normal ambient noise, and b) signal that the adaptive filter be restored to one of its prior states, from the copies stored in the state storage, when the disturbance detector detects abnormal noise; and an adaptive filter controller that is to update the state of the adaptive filter responsive to the state manager, wherein the state manager freezes the adaptive filter controller so that the controller stops updating the state of the adaptive filter, in response to the disturbance detector detecting abnormal noise, and wherein while the adaptive filter controller remains frozen, the ANC system is to produce anti-noise sound using the adaptive filter as configured into said one of its prior states.

2. The system of claim 1 wherein the disturbance detector is to a) detect normal ambient noise by detecting a primarily stationary acoustic disturbance, and b) detect abnormal noise by detecting a transient acoustic disturbance or tonal acoustic disturbance.

3. The system of claim 1 further comprising the adaptive filter whose state is defined at least in part by a set of digital filter coefficients, wherein the state storage is to store copies of prior sets of the digital filter coefficients.

4. The system of claim 3 wherein the adaptive filter models one of a primary noise path and a secondary path.

5. The system of claim 1 wherein the disturbance detector has an input to receive a signal from a reference microphone, a further input to receive a signal from an error microphone, and a further input to receive an additional signal, wherein the disturbance detector is to analyze the input signals to detect normal ambient noise and abnormal noise.

6. The system of claim 1 wherein when the disturbance detector is detecting normal ambient noise, the adaptive filter controller is in a known good state.

7. The system of claim 1 wherein the state manager unfreezes the adaptive filter controller in response to the disturbance detector detecting normal noise.

8. The system of claim 1 wherein the adaptive filter state storage stores each of the copies of prior states of the adaptive filter in association with a respective time stamp.

9. The system of claim 8 wherein the state manager is to select an earlier copy from the state storage, that will be used to restore the adaptive filter, when the latency of the disturbance detector is long, and a later copy when the latency of the disturbance detector is short.

10. The system of claim 8 wherein the disturbance detector is to receive a downlink signal and analyze it to detect far-end user speech therein, and the adaptive filter state storage is to store each of the copies of prior states in association with a flag that indicates whether or not the copy was written while downlink speech was determined to be present.

11. The system of claim 1 wherein the state manager is to perform a decision making process for selecting one of the copies of the prior states from the state storage, wherein the decision making process involves determining whether or not local speech activity is present when the disturbance detector indicates abnormal noise.

12. A method for managing the changing state of an adaptive filter in an active noise control (ANC) system, comprising:

producing anti-noise sound using the adaptive filter, while repeatedly updating state of the adaptive filter as time passes;

repeatedly writing a copy of a current state of the adaptive filter to storage as prior states, while normal ambient noise is being detected as time passes; and freezing the updating of the adaptive filter state in response to detecting abnormal noise and restoring the adaptive filter to one of its prior states, from the copies in the storage, when abnormal noise is detected such that the anti-noise sound is produced, using the adaptive filter as restored into said one of its prior states, while the updating of the adaptive filter state is frozen.

13. The method of claim 12 further comprising:

detecting normal ambient noise by detecting a primarily stationary acoustic disturbance; and detecting abnormal noise by detecting a transient acoustic disturbance or a tonal acoustic disturbance.

14. The method of claim 12 wherein detecting abnormal noise comprises monitoring an adaptive filter controller that is updating the state of the adaptive filter as time passes, and determining that the adaptive filter controller is in a known good state.

15. The method of claim 14 wherein the known good state is when the adaptive filter controller is exhibiting primarily steady state behavior without any substantial transient behavior.

16. The method of claim 12 further comprising:

unfreezing the updating of the adaptive filter state in response to detecting normal noise.

17. The method of claim 12 further comprising:

selecting an earlier copy from the storage, that is then used to restore the adaptive filter, when the latency associated with the abnormal noise detection is long, and a later copy when the latency is short.

18. The method of claim 12 wherein the copies of the current state of the adaptive filter that are written to storage are time stamped, the method further comprising:

selecting a copy from the storage, which is then used to restore the adaptive filter, that is closest in time to just before when a detection process began that detected the abnormal noise.

19. A system for managing the changing state of an adaptive filter in an active noise control (ANC) system, comprising:

means for repeatedly storing snapshots of the state of the adaptive filter as prior states while normal ambient noise, not abnormal noise, is being detected as time passes;

means for signaling that the adaptive filter be restored to one of its stored prior states and frozen in that prior state, when abnormal noise is detected; and means for producing anti-noise sound using the adaptive filter as restored into said one of its prior states and while frozen in that prior state.

20. The system of claim 19 further comprising the adaptive filter whose state is defined at least in part by a set of digital filter coefficients, wherein the storage means is to store copies of prior sets of the digital filter coefficients.

21. The system of claim 20 further comprising an adaptive filter controller that is to repeatedly update the state of the adaptive filter as time passes, unless it is signaled to freeze when abnormal noise is detected.

22. A system for managing the state of an adaptive filter in an active noise control (ANC) system, comprising:

an adaptive filter state storage that stores copies of prior states of the adaptive filter, wherein the adaptive filter produces an anti-noise signal of the ANC system;

a disturbance detector; and an adaptive filter state manager that a) signals that a copy of a current state of the adaptive filter be repeatedly written to the state storage while the disturbance detector is detecting normal ambient noise, wherein the adaptive filter state storage stores each of the copies of prior states of the adaptive filter in association with a respective time stamp, and b) signals that the adaptive filter be restored to a selected one of its prior states, from the copies stored in the state storage, when the disturbance detector detects abnormal noise so that an older prior state is selected if the disturbance detector is slow, and a younger prior state is selected if the disturbance detector is fast.

* * * * *